United States Patent
Djang

(10) Patent No.: US 8,765,193 B2
(45) Date of Patent: Jul. 1, 2014

(54) METHODS FOR RADIATION PROTECTION

(71) Applicant: Santé International, Inc., Jamestown, NY (US)

(72) Inventor: Arthur H. K. Djang, New York, NY (US)

(73) Assignee: Santé International, Inc., Jamestown, NY (US)

( * ) Notice: Subject to any disclaimer, the term of this patent is extended or adjusted under 35 U.S.C. 154(b) by 0 days.

(21) Appl. No.: 13/707,085

(22) Filed: Dec. 6, 2012

(65) Prior Publication Data

US 2014/0065247 A1 Mar. 6, 2014

Related U.S. Application Data

(60) Provisional application No. 61/634,215, filed on Feb. 24, 2012.

(51) Int. Cl.
| | | |
|---|---|---|
| *A61K 36/424* | (2006.01) | |
| *A61K 36/734* | (2006.01) | |
| *A61K 36/82* | (2006.01) | |
| *A61K 36/16* | (2006.01) | |
| *A61K 36/48* | (2006.01) | |

(52) U.S. Cl.
CPC ............ *A61K 36/82* (2013.01); *A61K 36/734* (2013.01); *A61K 36/424* (2013.01)
USPC ...................... 424/729; 424/725; 424/195.16

(58) Field of Classification Search
CPC .... A61K 36/424; A61K 36/734; A61K 36/82
See application file for complete search history.

(56) References Cited

U.S. PATENT DOCUMENTS

| | | | |
|---|---|---|---|
| 5,910,308 A * | 6/1999 | D'Jang | 424/729 |
| 6,168,795 B1 * | 1/2001 | DJang | 424/729 |
| 2003/0157203 A1* | 8/2003 | DJang | 424/729 |
| 2005/0208070 A1* | 9/2005 | Dao et al. | 424/195.15 |
| 2013/0101616 A1* | 4/2013 | Dao et al. | 424/195.15 |

OTHER PUBLICATIONS

Chadwick et al. (2011) J. Radiol. Prot. 31: 41-48.*
Kennedy (2009) Health Phys. 97(5): 433-445.*

* cited by examiner

*Primary Examiner* — Chris R Tate
*Assistant Examiner* — Russell Fiebig
(74) *Attorney, Agent, or Firm* — Jonathan M. D'Silva; MacDonald, Illig, Jones & Britton LLP

(57) ABSTRACT

Provided is a method for protecting an individual against radiation-induced internal damage that comprises administering an effective amount of an oral composition. The oral composition comprises a mixture of *Gynostemma pentaphyllum*, *Crataegus pinnatifida* (hawthorn), and *Camellia sinensis* (green tea) to an individual so that radiation-induced internal damage will be prevented or ameliorated.

12 Claims, No Drawings

METHODS FOR RADIATION PROTECTION

This application takes priority from U.S. Provisional Patent Application 61/634,215 filed on Feb. 24, 2012, which is incorporated herein by reference.

BACKGROUND

Radiation may be in the form of X-rays, gamma rays, alpha particles, beta particles, neutrons, and charged particles. Exposure to damaging or lethal radiation may result from a number of sources including, but not limited to, nuclear accidents, wartime or terrorist nuclear attack, therapeutic or diagnostic radiology, improper disposal of nuclear wastes, and outer space exploration. The extent of radiation-induced internal injury will depend on the duration, dose, and type of radiation exposure. Radiation-induced internal injury may include, but is not limited to, cell damage, and cell death; and may affect internal processes in the body such as the hematopoietic system (due to the reduction in number of hematopoietic cells such as lymphocytes, granulocytes, thrombocytes, and reticulocytes), gastrointestinal system (due to damage to epithelial cells lining the intestinal tract), and central nervous system (e.g., due to damage to neurons, astrocytes and blood vessels in the brain). What is provided is a method for protecting and a method for treating an individual against radiation-induced internal damage.

SUMMARY

A method is provided for protecting an individual against radiation-induced internal damage that comprises administering an effective amount of an oral composition. The oral composition comprises a mixture of *Gynostemma pentaphyllum*, *Crataegus pinnatifida* (hawthorn), and *Camellia sinensis* (green tea) to an individual so that radiation-induced internal damage will be prevented or ameliorated. One possible composition comprises about 10 to about 30 percent by weight of *Gynostemma pentaphyllum*, about 10 to about 30 percent by weight of *Camellia sinensis* (green tea), and about 40 to about 75 percent by weight of *Crataegus pinnatifida* (hawthorn). The composition could comprise a similar mixture of an aqueous extracts and alcohol extracts of those components in that proportion. The radiation treated under this method is an ionizing radiation selected from the group consisting of alpha radiation, beta radiation, gamma radiation, neutron radiation, X-ray and a combination thereof. It is possible for the method to be performed prophylactically where an effective amount is administered before exposure to radiation. This method could be administered at one or more times of during radiation exposure, and after radiation exposure. It is also possible for the oral composition to be administered in multiple doses. This method could also be administered to the individual prior to expected exposure to radiation, during exposure to radiation, or after exposure to radiation.

DETAILED DESCRIPTION

It will be understood that variations in the embodiments can generally be interchanged without deviating from the invention.

Definitions: While the following terms are believed to be well understood by one of ordinary skill in the art of biotechnology, the following definitions are set forth to facilitate explanation of the invention.

The "oral composition comprised of a mixture of *Gynostemma pentaphyllum*, *Crataegus pinnatifida*, and *Camellia sinensis*" comprises about 10 to about 30 percent by weight of *Gynostemma pentaphyllum*, about 10 to about 30 percent by weight of *Camellia sinensis* (green tea), and about 40 to about 75 percent by weight of *Crataegus pinnatifida* (hawthorn leaves and/or berries). Although there may be various methods to combine these ingredients, one method of making the oral composition is disclosed in U.S. Pat. No. 5,910,308. The composition comprises about 10 to about 30 percent by weight of *Gynostemma pentaphyllum* extract, about 10 to about 30 percent by weight of green tea extract, and about 40 to about 75 percent by weight of hawthorn extract. The preferred composition comprises about 10 to about 30 percent by weight of a mixture of an aqueous extract and an alcohol extract of *Gynostemma pentaphyllum*, about 10 to about 30 percent by weight of a mixture of an aqueous extract and an alcohol extract of green tea, and about 40 to about 75 per-cent by weight of a mixture of an aqueous extract and an alcohol extract of *Crataegus pinnatifida* (hawthorn leaves and/or berries). *Gynostemma pentaphyllum*, also known as 5-leaf ginseng or Jiaogulan or southern ginseng, is from the cucumber family and is rich in special saponins termed "gypenosides" some of which are similar, and some of which are different, to the ginsenosides found in ginseng, but at a level several fold higher. The leaves and berries of *Crataegus pinnatifida*, also known as hawthorn, contain saponins, flavonoids (including hyperoside), and anthocyanins (including proanthocyanidins). Leaves from the *Camellia sinensis* plant, particularly when processed into green tea, contain polyphenols including catechins such as epigallocatechin-3 gallate (EGCG), epigallocatechin, and epicatechin-3-gallate. While *Gynostemma pentaphyllum*, *Crataegus pinnatifida*, and *Camellia sinensis* have been used individually for health promoting and therapeutic purposes, not described is the ability of a composition comprising a mixture of *Gynostemma pentaphyllum*, *Crataegus pinnatifida* (hawthorn) and *Camellia sinensis* (green tea) to work together synergistically to protect an individual against radiation-induced internal damage. Optionally, the oral composition contains one or more carriers to facilitate one or more of formulation and administration.

The term "individual" is used herein, for purposes of the specification and claims, to mean an animal, preferably a mammal, and more preferably a human.

The term "radiation-induced internal injury" refers to injury or damage caused by radiation exposure, wherein the injury or damage is inside the body of an individual exposed to radiation; i.e., excluded is sunburn.

The term "ionizing radiation" is used herein, for purposes of the specification and claims, to mean radiation that has sufficient energy to eject one or more orbital electrons from an atom or molecule (e.g., $\alpha$ particles, $\beta$ particles, $\gamma$ particles, neutrons, protons, x-rays).

The terms "treatment" or "treating" are used herein, for purposes of the specification and claims, to mean administration of the oral composition in an amount that is effective in preventing, reducing or ameliorating radiation-induced injury to an individual who has been, is being, or will be exposed to radiation (thus, the oral composition being "radioprotective"). In the case that an individual will be exposed to radiation, the treatment is prophylactic (i.e., prior to radiation exposure, the oral composition is ingested by the individual using a prophylactically effective amount). In the case that that an individual is being or has been exposed to radiation, the treatment is therapeutic; i.e., after radiation exposure, the oral composition is ingested by the individual using a therapeutically effective amount.

Radiation-induced injury may include internal injury or internal damage to the human body caused by exposure to radiation. Such internal injury may include, but is not limited to, bone marrow cell damage, intestinal damage, damage to the central nervous system, DNA mutations causing cell injury and/or death, and development of cancer. The methods are particularly useful for treating an individual (including a single individual or more than one individual) engaging in activities involving a high risk of radiation exposure. Also, the methods can be used to treat individuals exposed to radiation so as to prevent or ameliorate radiation-induced injury. Exposure to radiation may be a result of radiation emanating from radioactive materials released by terrorists or as a result of a nuclear accident, from diagnostic machines such as an X-ray machine, a C-T scanner, or a synchrotron, from therapeutic radiation (e.g., intended to kill cancer cells, wherein the radiation-induced injury to be prevented or ameliorated is to the nonmalignant tissue, surrounding or adjacent to the tumor intended to be killed by radiation).

For use in a method, the oral composition is formulated in any acceptable oral dosage form, including but not limited to, a tablet, pill, caplet, capsule, lozenge, powder, solution, suspension, and the like for ingestion. Oral compositions comprising a tablets, pills, caplets, capsules, or lozenges generally include carrier. Such a carrier may include one or more of a binder (e.g., such as, but not limited to, polyol, microcrystalline cellulose, gelatin, gum such as arabic or tragacanth, etc.), an excipient (e.g., such as, but not limited to, starch, lactose, calcium carbonate, sodium citrate, calcium phosphate, etc.), a disintegrant (e.g., such as, but not limited to, alginic acid, corn starch, silicates, etc.), a lubricating agent (e.g., such as, but not limited to, talc, sodium lauryl sulfate, magnesium stearate or other stearates, etc.), a coating (e.g., such as, but not limited to, lecithin, etc.), and a flavoring agent (e.g., a sweetener such as a carbohydrate, sugar alcohol, saccharin, aspartame, stevia, and the like; or fruit or mint flavoring). Where the oral composition is liquid in nature or containing a liquid, the carrier may be a solvent or dispersion medium including but not limited to one or more of an inert diluent, water, an alcohol, an edible oil, and a syrup.

In the method for protecting an individual against radiation-induced internal damage, the oral composition comprising a mixture of *Gynostemma pentaphyllum, Crataegus pinnatifida*, and *Camellia sinensis* is administered to an individual that may be potentially exposed to radiation (e.g., as a result of engaging in an activity that has a high risk of radiation exposure), an individual that is in the process of being exposed to radiation, or an individual who has already been exposed to radiation. The effective amount of the oral composition to administer to the individual in the method will vary depending on several factors including, but not limited to, the age, general health, and body weight of the individual at the time of administration; and the severity of the radiation exposure, expected radiation exposure, or apparent radiation-induce injury. Additionally, an effective dose may be determined by standard pharmaceutical procedures such as using cell cultures, or experimental in vivo models, and by the medical profession (e.g., doctor, nurse, pharmacist, pharmacologist, etc.) taking into consideration factors relating to the individual in need of treatment.

The radioprotective oral composition may be administered once per day, or multiple times (e.g., 2 to 5 times) per day, as needed, more preferably 2 to 3 times per day, as needed, or 3 times per day, to an individual in need of such treatment. Preferably, during each administration of a dose, 1 to 3 tablets, caplets, capsules, pills or other form of the oral composition are ingested by the individual in need of treatment. The active ingredients in the oral composition are components in the 5 mixture of *Gynostemma pentaphyllum, Crataegus pinnatifida*, and *Camellia sinensis*. A dosage amount of the oral composition for each administration may contain from about 0.1 gram to about 1 gram of the active ingredients, and more preferably from about 0.2 grams to about 0.75 grams of the active ingredients.

The examples presented herein are intended to be illustrative in nature, and in no way intended to limit the scope of the claimed methods and discussed in detail above. In these examples, four methods were used to illustrate a method; i.e., use of an oral composition comprising a mixture of *Gynostemma pentaphyllum, Crataegus pinnatifida*, and *Camellia sinensis* can work synergistically to prevent or ameliorate radiation-induced injury or damage. Bone marrow failure is the major cause of radiation lethality in mammals. An accepted and standard indirect method to determine the consequences of damage to marrow resulting from radiation exposure includes measurement of peripheral blood cells, wherein reductions in peripheral blood cell counts reflect radiation damage.

The second method utilized in this assessment is the micronucleus assay. Ionizing radiation is a strong clastogenic agent, and thus a potent inducer of micronuclei (chromosomal aberrations, typically the result of unrepaired or misrepaired double-strand DNA breaks). The micronucleus assay quantifies radiation-induced chromosome damage expressed as post-mitotic micronuclei. Many studies have shown that the number of radiation-induced micronuclei is strongly correlated with dose and type of radiation. Thus, the micronucleus assay has become a validated and standard technique for evaluating in vivo radiation exposure of individuals, as well as for determining the radioprotective effect of a test compound.

The third method used to illustrate a method of the invention is the comet assay or single cell gel-electrophoresis assay. The assay is based on the embedding of cells in agarose, followed by cell lysis, and subsequent electrophoresis. The electric current pulls the charged DNA from the nucleus, where broken DNA fragments migrate further from the nucleus than intact DNA. The resultant pattern, named for its resemblance to comets, is used to measure and determine the extent of DNA damage. For example, it is known that comet parameters such as tail length, tail moment, and percent of DNA in tail were increased in the blood leukocytes exposed to high γ-radiation. When a radioprotective agent is administered before the radiation exposure, the increase in the comet parameters as a result of radiation was prevented, indicating a protection of cellular DNA. Thus, the comet assay is a validated and standardized technique for determining the radioprotective effect of a test compound.

The fourth method is measurement of total antioxidant capacity (T-AOC). It is known that ionizing radiation exposure induces free radicals which damage cells. Scavenging of free radicals produced from radiation exposure can protect cells from radiation-induced injury or death. This assay can be used to ascertain whether or not the mechanism of action of a radioprotectant involves free radical scavenging.

EXAMPLE 1

In this Example, illustrated are methods of radioprotection using an oral composition comprising a mixture of *Gynostemma pentaphyllum, Crataegus pinnatifida*, and Camellia sinensis to treat radiation-induced injury or damage in standard models for determining a radioprotective effect. Male BALB/c mice, weighting from 22 g to 28 g, were divided into a two groups. A "treatment" group was pre-treated by administering an oral composition comprising a mixture of Gynostemma pentaphyllum, Crataegus pinnatifida, and Camellia sinensis. The oral composition, comprising a mixture of Gynostemma pentaphyllum, Crataegus pinnatifida, and Camellia sinensis as previously described herein in more detail, that was used in these experiments is commercially available (ONCOLYN®). Mice in the treatment group were treated with the oral composition at dose of 500 mg/kg for 7 days by oral gavage. The "control" group of mice was administered distilled water as the same volume and timing as was administered the oral composition to the treatment group.

Whole body irradiation of each of the treatment group and control group was performed with an X-ray source. Mice were placed in ventilated caged and irradiated in groups of five mice simultaneously. The source to skin distance was 100 cm with a dose rate of 300 cGy/min at room temperature. The mice were irradiated with a total dose of 1.5 Gy or 3.0 Gy. At 24 hours after irradiation, mice were anesthetized. Blood samples were taken from abdominal aorta. 0.5 ml blood was put into heparin for anticoagulation. Blood cell classification and counting were performed using an automated cell analyzer. As shown in Table, 1, a method of the invention for protecting an individual against radiation-induced internal damage comprises administering the oral composition comprising a mixture of Gynostemma pentaphyllum, Crataegus pinnatifida, and Camellia sinensis to an individual that is subsequently exposed to radiation. As shown in Table 1, the treatment group (receiving the oral composition comprising a mixture of Gynostemma pentaphyllum, Crataegus pinnatifida, and Camellia sinensis) prior to radiation exposure showed a radioprotective effect as evident by a significantly increased number of peripheral blood cells as compared to that of the control group which received the corresponding dose of radiation but did not receive treatment with the oral composition. In Table 1, the total number of cells counted is expressed in $10^9$/L, wherein "WBC" is the white blood cell count; "GRAN" is the granulocyte count; "LYM" is the lymphocyte count; "MID" is the count of less frequently occurring and rare cells correlating to monocytes, eosinophils, basophils, blasts and other precursor white cells.

TABLE 1

Radiation-induced internal damage of bone marrow, as measured by peripheral blood cell counts

| Groups | WBC | GRAN | LYM | MID | platelets |
|---|---|---|---|---|---|
| No radiation | 10.89 ± 1.19 | 1.54 ± 0.38 | 5.13 ± 1.24 | 1.74 ± 0.47 | 578.60 ± 71.50 |
| 3.0Gy Control | 4.47 ± 0.87* | 0.67 ± 0.19* | 2.80 ± 0.57* | 0.84 ± 0.19* | 313.25 ± 67.67* |
| 3.0Gy Treatment | 8.53 ± 0.92* | 1.81 ± 0.32# | 5.08 ± 1.08* | 1.78 ± 0.51# | 415.14 ± 55.25* |
| 1.5Gy Control | 7.32 ± 1.36* | 1.03 ± 0.24* | 4.75 ± 0.79 | 1.08 ± 0.23* | 494.16 ± 82.83 |
| 1.5Gy Treatment | 10.40 ± 2.01* | 1.65 ± 0.31# | 5.36 ± 1.06 | 1.87 ± 0.64* | 503.57 ± 84.33 |

Notes:
*control group compared with non-radiated animals $p < 0.05$;
treatment group compared with control group and at the corresponding radiation dose $p < 0.05$.

A standard comet assay was performed from the blood samples collected. The entire assay was conducted under low indirect incandescent light (60 Watts) to minimize light-induced damage to lymphocyte DNA. Two fully-frosted microscopic slides per sample were prepared. Each slide was covered with 100 μl of 1% normal melting agarose at about 42° C. in phosphate buffered saline (PBS), and the gel was immediately covered with a cover slip and kept for 20 minutes in a refrigerator to solidify. After gently removing the cover slip, 100 μl mixture of 30 μl blood sample in PBS and 90 μl of 1% low melting agarose was rapidly add onto the agarose layer, and then spread using a cover slip. The cover slips were then removed, and the slides were submersed in freshly prepared cold lysis solution (2.5 M NaCl, 100 mM $Na_2EDTA$, 10 mM Tris base, with freshly added 1% Triton X-100 and 10% DMSO, pH=10) at 4° C. for at least 1 hour. Slides were then placed in a horizontal electrophoresis tank with freshly prepared alkaline electrophoresis solution (1 mM $Na_2EDTA$, 300 mM NaOH, pH>13) for 30 minutes at 4° C. to allow the unwinding of the DNA, and expression of alkali-labile site, before being electrophoresed under neutral conditions at 12 volts and 300 milliamps for 30 minutes at room temperature using an electrophoresis compact power supply. When put in an electrical field, the intact DNA was such a large molecule that it hardly moved. DNA breaks, however, lead to smaller pieces of DNA which migrated away from the intact DNA. After electrophoresis, the slides were equilibrated in neutral solution (300 mM sodium acetate, 100 mM Tris, pH 9) for 5 minutes. The slides were stained with ethidium bromide (20 mgl$^{-1}$, 35 μl/slide). Quantification of DNA damage was assessed in over 100 cells in the center of each gel, by using a microscope (equipped with a 100-W mercury lamp and WG filter block), and taking pictures at 400× magnification. The cells containing damaged DNA had the appearance of a comet with a bright head (undamaged) and tail. Measurements of Comet parameters included presence of comets, tail length. About 1000 cells from each slide were examined by comet image analysis software was used to measure comet extent (tail length) and percentage of comet cells. Comet extent is a measure of total comet length from the beginning of the head to the last visible pixel in the tail. The percentage of comet cells is calculated by dividing the comet cell number counted in 100 lymphocytes per slide by 100 lymphocytes.

A standard micronucleus assay was performed. Peripheral blood cells were smeared, and then immediately stained with a DNA specific stain (e.g., acridine orange). The proportion of immature among total (immature+mature) erythrocytes is determined for each animal by counting a total of at least 1000 erythrocytes for peripheral blood. At least 2000 immature erythrocytes per animal are scored for the incidence of micronucleated immature erythrocytes.

As shown in Table 2, a method for protecting an individual against radiation-induced internal damage comprises administering the oral composition comprising a mixture of Gynostemma pentaphyllum, Crataegus pinnatifida, and Camellia sinensis to an individual. As shown in Table 2, as compared to the control group with the corresponding radiation exposure, treatment with the oral composition resulted in a significant reduction in the treatment group of the: (a) number of micronucleated cells; (b) percentage of comet cells; and (c) tail length of comet cells (i.e., demonstrated is a radioprotective effective).

TABLE 2

Radiation-induced internal damage, as measured by micronucleus assay and by the comet assay.

| Groups | Micronucleated cells (‰) | % comet cells | Tail length of comet cells (μm) |
|---|---|---|---|
| no radiation | 2.83 ± 0.75 | 4.2 ± 0.91 | 11.45 ± 2.56 |
| 3.0Gy X-ray control | 19.5 ± 5.68* | 42.67 ± 7.88* | 42.67 ± 6.58 |
| 3.0Gy X-ray treatment | 11.14 ± 4.89# | 25.47 ± 5.46# | 27.19 ± 4.73 |
| 1.5Gy X-ray control | 14.67 ± 4.12* | 30.13 ± 7.94* | 31.56 ± 5.33 |
| 1.5Gy X-ray treatment | 9.50 ± 3.03# | 17.68 ± 6.39# | 22.20 ± 4.11 |

Notes:
*control group compared with non-irradiated animals, $p < 0.05$;
treatment group compared with the control group of the corresponding radiation dose, $p < 0.05$ A commercially available assay for measuring total antioxidant capacity was used. Briefly, serum from mice of a control group or from mice of a treatment group is mixed with a reagent containing pholasin, and incubated for 30 minutes at 37° C. Antioxidants can reduce $Fe^{3+}$ to $Fe^{2+}$, and $Fe^{2+}$ binds with pholasin which produces a visible chelating agent measurable at an absorption of 520 nm. An increase in 0.01 of the absorption value per minute per milliliter serum was determined as a unit of total antioxidant capacity. Total antioxidant capacity unit=[(Optical Density of the determined tube−Optical Density of the assay control tube)×N×n] 0.01; wherein "N" is the diluted fold in the reaction system (total volume of reaction/serum sample volume), and "n" is the fold dilution of sample. As shown in Table 3, a method for protecting an individual against radiation-induced internal damage comprises administering the oral composition comprising a mixture of Gynostemma pentaphyllum, Crataegus pinnatifida, and Camellia sinensis to an individual. As shown in Table 3, as compared to the control group with the corresponding radiation exposure, treatment with the oral composition at the higher doses of radiation (e.g., 3.0 Gy) resulted in a significant increase in the total antioxidant capacity in the treatment group. This suggests that at radiation doses approaching 3.0 Gy or greater, the free radical scavenging (antioxidant activity) of the oral composition is contributing to the method of protecting against radiation-induced internal damage. The results also suggest that after certain doses of radiation exposure (e.g., 1.5 Gy), the mixture in the oral composition works synergistically by mechanisms in lieu of or in addition to free radical scavenging in protecting an individual from radiation-induced internal injury or damage. Such other mechanism(s) could include, but is not limited to: protecting DNA from radiation-induced damage; enhancing repair of DNA damage induced by radiation; inhibiting apoptotic pathway(s) induced by radiation or radiation-induced damage; inhibiting radiation-induced activation of cell signaling pathways; activating of radiation-induced inhibition of cell signaling pathways; or a combination thereof.

TABLE 3

Measurement in serum of total antioxidant capacity (T-AOC)

| Groups | T-AOC(U/ml) |
|---|---|
| No radiation | 11.99 ± 3.66 |
| 1.5Gy X-ray control | 9.18 ± 3.04 |
| 1.5Gy X-ray treatment | 9.46 ± 1.89 |

TABLE 3-continued

Measurement in serum of total antioxidant capacity (T-AOC)

| Groups | T-AOC(U/ml) |
|---|---|
| 3.0Gy X-ray control | 7.03 ± 1.82* |
| 3.0Gy X-ray treatment | 12.26 ± 2.42# |

Notes:
*compared with non-irradiated animals (assay control) $p < 0.05$;
Treatment group compared with the corresponding X-ray Control group $p < 0.05$

EXAMPLE 2

In this Example, illustrated are methods of radioprotection using an oral composition comprising a mixture of Gynostemma pentaphyllum, Crataegus pinnatifida, and Camellia sinensis to treat radiation-induced internal injury or damage in an individual for determining a radioprotective effect. Eight human volunteers, aging from 25 years to 30 years in age, gave blood samples, and then took 1 gram of an oral composition, comprising a mixture of Gynostemma pentaphyllum, Crataegus pinnatifida, and Camellia sinensis as previously described herein in more detail. Following the administration of the oral composition, the human volunteers gave blood samples at 1 hour and also at 3 hours post treatment with the oral composition. All blood samples were then subjected to radiation exposure (1.5 Gy γ-radiation). A portion of each blood sample was used for a comet assay test, and the remainder of each blood sample was used for the micronucleus test (using the assay protocols essentially described in Example 1 herein).

For the comet assay, the lymphocytes were separated from polymorphonuclear leucocytes and erythrocytes contained in the heparinized whole blood sample, and the lymphocytes were then washed twice and suspended in 500 μl ice-cold phosphate-buffered saline (PBS). The comet assay was performed on the lymphocytes isolated from each blood sample. As shown in Table 4, a method for protecting an individual against radiation-induced internal damage comprises administering the oral composition comprising a mixture of Gynostemma pentaphyllum, Crataegus pinnatifida, and Camellia sinensis to an individual. As shown in Table 4 and Table 5, as compared to the control group with the corresponding radiation exposure, treatment with the oral composition resulted in a significant reduction in the treatment group of the: (a) percentage of comet cells; and (b) tail length of comet cells (i.e., demonstrated is a radioprotective effective). In Table 4 and Table 5, "Individual" represents the different individuals who gave blood samples for treatment; "baseline", represents comet assay results on blood samples which were not exposed to radiation nor treatment; "γ ray control" represents comet assay results from blood samples exposed to radiation but not treated; and "γ ray post treatment" represents comet assay results from blood samples from individuals treated with the oral composition, which blood samples were subsequently exposed to radiation after the designated number of hours.

TABLE 4

Radiation-induced internal damage, as measured by comet cell number (%)

| (%) Individual | baseline | γ ray control | γ ray post treatment 1 hours | γ ray post treatment 3 hours |
|---|---|---|---|---|
| 1 | 5.2 ± 1.1 | 62.57 ± 15.44 | 40.12 ± 8.57* | 22.66 ± 6.12*# |
| 2 | 4.8 ± 0.92 | 58.79 ± 11.09 | 41.23 ± 9.66* | 23.58 ± 5.72*# |
| 3 | 5.7 ± 1.1 | 59.87 ± 10.38 | 38.64 ± 7.38* | 19.67 ± 8.97*# |
| 4 | 5.7 ± 1.0 | 61.72 ± 15.44 | 42.71 ± 9.37 | 25.41 ± 6.77*# |
| 5 | 6.2 ± 1.3 | 68.99 ± 17.78 | 46.35 ± 9.16* | 27.32 ± 5.64*# |
| 6 | 5.0 ± 1.3 | 54.12 ± 10.23 | 34.72 ± 6.97* | 18.67 ± 5.12*# |
| 7 | 5.2 ± 1.4 | 56.38 ± 8.67 | 39.66 ± 7.82* | 19.68 ± 7.53*# |
| 8 | 5.8 ± 1.5 | 61.46 ± 14.55 | 40.19 ± 9.68* | 20.18 ± 3.22*# |

Notes:
*post treatment group compared with γ ray control group, $p < 0.05$;
post treatment 3 hour group compared with γ ray control group and with γ ray post treatment- 1 hour group, $p < 0.05$

TABLE 5

Radiation-induced internal damage, as measured by tail length of comet cells (μm)

| Individual | baseline | γ ray control | γ ray post treatment 1 hour | γ ray post treatment 3 hours |
|---|---|---|---|---|
| 1 | 10.45 ± 2.56 | 72.35 ± 15.12 | 49.67 ± 6.58* | 32.19 ± 4.73*# |
| 2 | 11.23 ± 2.35 | 68.95 ± 14.32 | 47.26 ± 7.85* | 29.67 ± 5.06*# |
| 3 | 10.72 ± 3.01 | 71.26 ± 16.38 | 46.28 ± 6.57 | 25.64 ± 6.31*# |
| 4 | 11.38 ± 1.47 | 70.23 ± 14.89 | 48.67 ± 8.77 | 27.09 ± 5.68*# |
| 5 | 12.59 ± 2.84 | 69.26 ± 10.22 | 47.66 ± 8.31* | 22.59 ± 6.80*# |
| 6 | 10.67 ± 1.29 | 70.43 ± 11.76 | 42.39 ± 8.05* | 21.38 ± 4.52*# |
| 7 | 10.98 ± 2.03 | 67.91 ± 16.34 | 46.12 ± 9.60* | 24.31 ± 5.30*# |
| 8 | 11.65 ± 2.31 | 68.55 ± 10.33 | 41.28 ± 6.38* | 22.37 ± 6.01*# |

Notes:
*post treatment group compared with γ ray control group, $p < 0.05$;
post treatment 3 hour group compared with γ ray control group and with γ ray post treatment- 1 hour group, $p < 0.05$ This invention has been described with reference to several preferred embodiments. Many modifications and alterations will occur to others upon reading and understanding the preceding specification. It is intended that the invention be construed as including all such alterations and modifications in so far as they come within the scope of the appended claims or the equivalents of these claims.

What is claimed is:

1. A method for protecting in a non-tumor bearing individual against radiation-induced non-cancerous internal damage comprising administering to the individual an effective amount of an oral composition comprising about 10 to about 30 percent by weight of a mixture of an aqueous extract and an alcohol extract of *Gynostemma pentaphyllum*, about 10 to about 30 percent by weight of a mixture of an aqueous extract and an alcohol extract of *Camellia sinensis* (green tea), and about 40 to about 75 percent by weight of a mixture of an aqueous extract and an alcohol extract of *Crataegus pinnatifida* (hawthorn berries) so that radiation-induced non-cancerous internal damage is attenuated or ameliorated.

2. The method according to claim 1 wherein the radiation is ionizing radiation selected from the group consisting of alpha radiation, beta radiation, gamma radiation, neutron radiation, X-ray and a combination thereof.

3. The method according to claim 1, wherein the effective amount of the oral composition is administered before the individual is exposed to radiation.

4. The method according to claim 1 wherein the effective amount is a therapeutically effective amount administered at one or more times of during radiation exposure, and after radiation exposure.

5. The method according to claim 1 wherein the oral composition is administered in multiple doses.

6. The method according to claim 1 wherein the radiation-induced noncancer internal damage comprises bone marrow cell damage, intestinal damage, damage to the central nervous system, or DNA mutations causing cell injury or cell death.

7. A method of treating in a non-tumor bearing individual against radiation-induced non-cancerous internal injury, the method comprising administering to the individual prior to expected exposure to radiation, during exposure to radiation, or after exposure to radiation, an oral composition comprising about 10 to about 30 percent by weight of a mixture of an aqueous extract and an alcohol extract of *Gynostemma pentaphyllum*, about 10 to about 30 percent by weight of a mixture of an aqueous extract and an alcohol extract of *Camellia sinensis* (green tea), and about 40 to about 75 percent by weight of a mixture of an aqueous extract and an alcohol extract of *Crataegus pinnatifida* (hawthorn berries) in an amount effective to attenuate or treat radiation-induced non-cancerouis internal injury.

8. The method according to claim 7 wherein the radiation is ionizing radiation selected from the group consisting of alpha radiation, beta radiation, gamma radiation, neutron radiation, X-ray and a combination thereof.

9. The method according to claim 1, wherein the effective amount of the oral composition is administered before the individual is exposed to radiation.

10. The method according to claim 7 wherein the effective amount is a therapeutically effective amount administered one or more times of during radiation exposure, and after radiation exposure.

11. The method according to claim 7 wherein the oral composition is administered in multiple doses.

12. The method according to claim 7 wherein the radiation-induced noncancerous internal damage comprises bone marrow cell damage, intestinal damage, damage to the central nervous system, or DNA mutations causing cell injury or cell death.

* * * * *